(12) United States Patent
Wang et al.

(10) Patent No.: US 9,381,196 B2
(45) Date of Patent: *Jul. 5, 2016

(54) COMPOUNDS, PHARMACEUTICAL COMPOSITIONS AND METHODS OF USE OF HYDROXAMIC ACID DERIVATIVES

(71) Applicant: THE TRANSLATIONAL GENOMICS RESEARCH INSTITUTE, Phoenix, AZ (US)

(72) Inventors: Tong Wang, Scottsdale, AZ (US); Stephen Gately, Scottsdale, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 45 days.

This patent is subject to a terminal disclaimer.

(21) Appl. No.: 14/663,180

(22) Filed: Mar. 19, 2015

(65) Prior Publication Data

US 2015/0196559 A1 Jul. 16, 2015

Related U.S. Application Data

(63) Continuation of application No. 12/865,903, filed as application No. PCT/US2009/032917 on Feb. 3, 2009, now Pat. No. 8,987,468.

(60) Provisional application No. 61/025,861, filed on Feb. 4, 2008.

(51) Int. Cl.
| | |
|---|---|
| *A01N 37/28* | (2006.01) |
| *A61K 31/19* | (2006.01) |
| *A61K 31/506* | (2006.01) |
| *C07D 235/16* | (2006.01) |
| *C07D 403/04* | (2006.01) |
| *A61K 31/4184* | (2006.01) |
| *A61K 31/437* | (2006.01) |
| *A61K 45/06* | (2006.01) |

(52) U.S. Cl.
CPC ........... *A61K 31/506* (2013.01); *A61K 31/4184* (2013.01); *A61K 31/437* (2013.01); *A61K 45/06* (2013.01); *C07D 235/16* (2013.01); *C07D 403/04* (2013.01)

(58) Field of Classification Search
None
See application file for complete search history.

(56) References Cited

U.S. PATENT DOCUMENTS 5,804,601 A * 9/1998 Kato et al. ............. 514/563

OTHER PUBLICATIONS

Neidle, Cancer Drug Design and Discovery, Elsevier/Academic Press, 2008, pp. 427-431.*

* cited by examiner

*Primary Examiner* — Jeffrey S Lundgren
*Assistant Examiner* — Stephanie Springer

(57) ABSTRACT

The invention encompasses a compound derived from hydroxamic acid that may be used to slow the expansion of cancer cells and thus is effective in the treatment of cancer. Generally, the disclosed compound includes a benzimidazole group coupled to a hydroxyamide of five or more unsubstituted carbon atoms and any pharmaceutically acceptable salts, solvates and chemically protected forms thereof. Also disclosed are pharmacological compositions including the compound and methods of using the compound to slow the expansion of cancer cells as well as methods of using the compound to treat cancer.

7 Claims, 1 Drawing Sheet

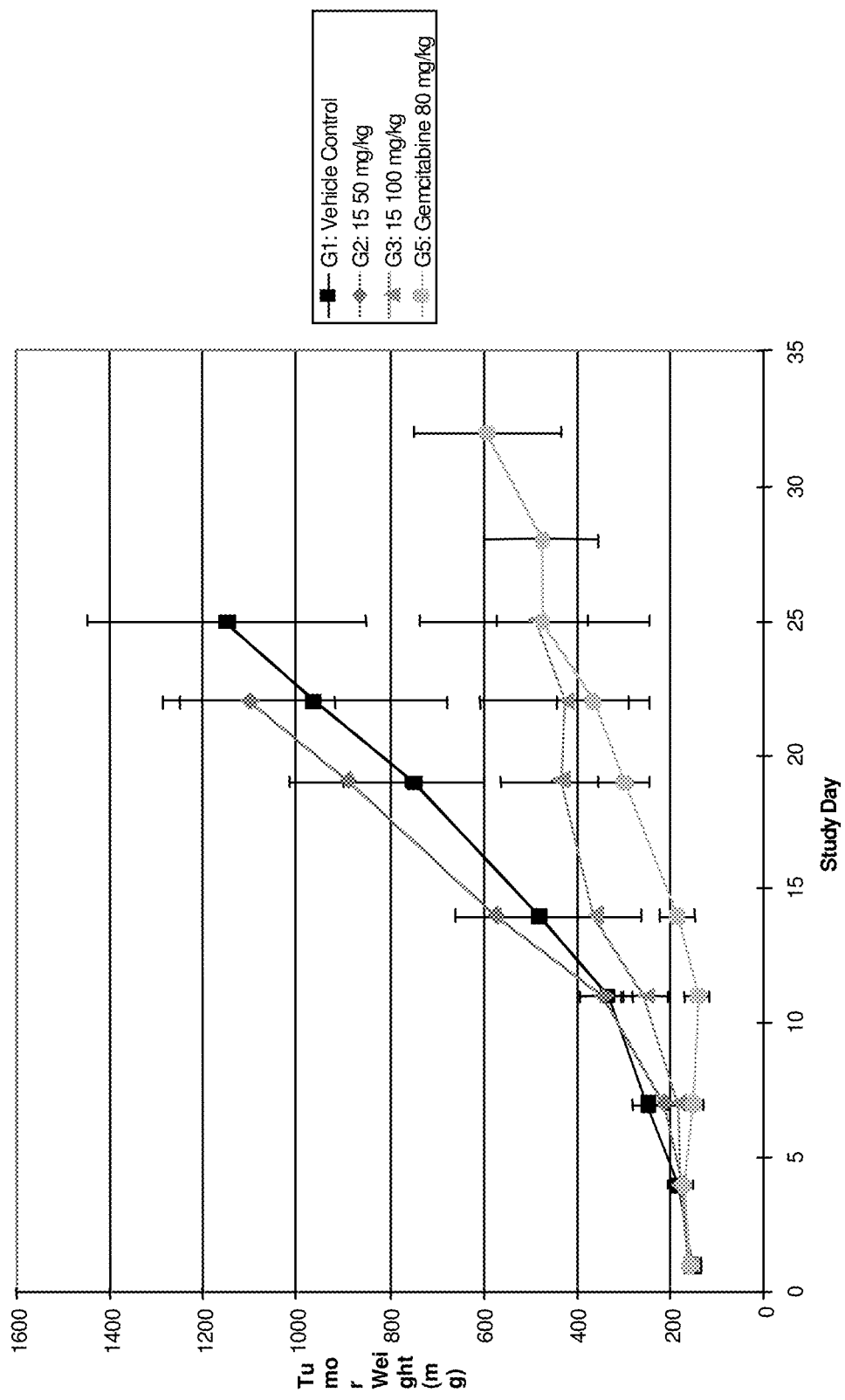

COMPOUNDS, PHARMACEUTICAL COMPOSITIONS AND METHODS OF USE OF HYDROXAMIC ACID DERIVATIVES

CROSS REFERENCE TO RELATED APPLICATION

This application is a continuation application of U.S. non-provisional patent application Ser. No. 12/865,903, filed Aug. 3, 2010, which is the national stage of International Patent Application No. PCT/US2009/032917, filed on Feb. 3, 2009, which claims the priority of U.S. provisional application with application No. 61/025,861 filed Feb. 4, 2008, the contents of each of which are hereby incorporated by reference in their entirety for all purposes.

BACKGROUND OF THE INVENTION

Generally, the invention pertains to the field of pharmaceutical compounds and more specifically to the field of hydroxamic acid derivatives useful in the treatment of cancer. Cancer is the second leading cause of death in the United States and despite new breakthroughs that have led to decreased mortality, many cancers remain refractory to treatment. Additionally, typical treatments such as chemotherapy, radiotherapy and surgery cause a broad spectrum of undesirable side effects. In addition, many cancers often develop resistance to current chemotherapies over time. Clearly the field is in significant need of novel compounds and methods of slowing the expansion of cancer cells and that are useful in the treatment of cancer.

So as to reduce the complexity and length of the Detailed Specification, and to fully establish the state of the art in certain areas of technology, Inventors herein expressly incorporate by reference all of the following materials identified in each numbered paragraph below. The incorporated materials are not necessarily "prior art" and Inventors expressly reserve the right to swear behind any of the incorporated materials.

1. Pisano et al, WO 2006/131484, filed May 31, 2006.
2. Finn et al, US 2006/0079528, filed Feb. 25, 2004.
3. Baxter et al, WO 2000/69827, filed May 12, 1999.
4. Kato et al, EP 0 737 671, filed Apr. 10, 1995.
5. Lafon, U.S. Pat. No. 4,122,186 filed Oct. 24, 1978.
6. Paris et al, "Histone Deacetylase Inhibitors: From Bench to Clinic" J. Med. Chem Vol. 51, No. 6 pp. 1505-1529 (Mar. 27, 2008.)
7. Miller T A et al, "Histone Deacetylase Inhibitors" J. Med. Chem. Vol. 46 No. 24 pp. 5097-5116 (2003.)
8. Guines H S et al, "Synthesis of some hydroxamic acid derivatives of benzimidazole and their antibacterial and antifungal activities" Arzneimittel-Forschung Vol. 42 No. 8, pp 1045-1048 (1992).

The Inventors believe that the material incorporated above is "non-essential" in accordance with 37 CFR 1.57, because it is referred to for purposes of indicating the background of the invention or illustrating the state of the art. However, if the Examiner believes that any of the above-incorporated material constitutes "essential material" within the meaning of 37 CFR 1.57(c)(1)-(3), Inventors will amend the specification to expressly recite the essential material that is incorporated by reference as allowed by the applicable rules.

SUMMARY OF THE INVENTION

The present invention provides among other things a pharmaceutical compound effective in the treatment of cancer.

It is an object of the invention to provide a pharmaceutical compound that slows the expansion of cancer cells.

It is an object of the invention to treat ovarian cancer.
It is an object of the invention to treat pancreatic cancer.
It is an object of the invention to treat breast cancer.
It is an object of the invention to treat non-small cell lung cancer
It is an object of the invention to treat adrenocortical carcinoma
It is an object of the invention to treat lung adenocarcinoma
It is an object of the invention to treat prostate cancer.

The above and other objects may be achieved using a compound with the formula

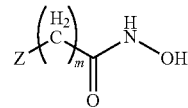

including all pharmaceutically acceptable salts thereof. The group denoted Z is a group with the formula:

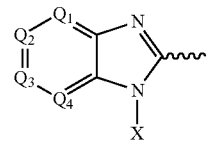

The group denoted X may be any of the following: H, —$C_1$-$C_6$ alkyl, aryl, —$C_3$-$C_7$ cycloalkyl, or —3- to 10-membered heterocycle, any of which may be unsubstituted or substituted with one or more of the following; -halo, —$C_1$-$C_6$ alkyl, —O—($C_1$-$C_6$ alkyl), —OH, —CN, —COOR', —OC(O)R', NHR', N(R')$_2$, —NHC(O)R' or —C(O)NHR' groups wherein R' may be —H or —$C_1$-$C_6$ alkyl.

The groups denoted $Q_1$, $Q_2$, $Q_3$, and $Q_4$ may be carbon or nitrogen coupled to any of the following: —H, —$C_1$-$C_6$ alkyl, aryl, —$C_3$-$C_7$ cycloalkyl or 3- to 10-membered heterocycle, any of which may be unsubstituted or substituted with one or more -halo, —$C_1$-$C_6$ alkyl, —O—($C_1$-$C_6$ alkyl), —OH, —CN, —COOR', —OC(O)R', NHR', N(R')$_2$, —NHC(O)R' or —C(O)NHR' groups wherein R' may be —H or any —$C_1$-$C_6$ alkyl. The groups denoted by $Q_1$, $Q_2$, $Q_3$, and $Q_4$ are independently selected. The number denoted by m is any integer greater than 4. In some aspects of the invention the number denoted by m is an integer greater than 4 and less than 11. In some aspects of the invention, $Q_1$, $Q_3$, and $Q_4$ are all C—H groups while $Q_2$ is a C-aryl group (substituted or unsubstituted,) or a C-halo group such as Cl or Br. The invention further encompasses all pharmaceutically acceptable salts, solvates, and chemically protected forms comprising the compound.

The above and other objects may be achieved by methods involving arresting the growth of tumors with an effective amount of a pharmaceutical composition that includes the disclosed compound and, in some aspects of the invention, one or more pharmaceutically acceptable carriers.

The above and other objects may be achieved by methods involving treating a mammal with an effective amount of a pharmaceutical composition that includes the disclosed compound and, in some aspects of the invention, one or more pharmaceutically acceptable carriers.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts. The Inventors are fully aware that they can be their own lexicographers if desired. The Inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the Inventors' intent and desire that the simple, plain and ordinary meaning to the terms be applied to the interpretation of the specification and claims.

The Inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the Inventors are fully informed of the standards and application of the special provisions of 35 U.S.C. §112, ¶16. Thus, the use of the words "function," "means" or "step" in the Detailed Description or Description of the Drawings or claims is not intended to somehow indicate a desire to invoke the special provisions of 35 U.S.C. §112, ¶16, to define the invention. To the contrary, if the provisions of 35 U.S.C. §112, ¶16 are sought to be invoked to define the inventions, the claims will specifically and expressly state the exact phrases "means for" or "step for, and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the Inventors not to invoke the provisions of 35 U.S.C. §112, ¶16. Moreover, even if the provisions of 35 U.S.C. §112, ¶16 are invoked to define the claimed inventions, it is intended that the inventions not be limited only to the specific structure, material or acts that are described in the preferred embodiments, but in addition, include any and all structures, materials or acts that perform the claimed function as described in alternative embodiments or forms of the invention, or that are well known present or later-developed, equivalent structures, material or acts for performing the claimed function.

Elements and acts in the figures are illustrated for simplicity and have not necessarily been rendered according to any particular sequence or embodiment.

BRIEF DESCRIPTION OF THE DRAWINGS

A more complete understanding of the present invention may be derived by referring to the detailed description when considered in connection with the following illustrative figure.

FIG. 1 depicts the results of a study in which 7-(5-bromo-1H-benzimidazol-2-yl)-N-hydroxyheptanamide (Compound ID #15) was used to shrink tumors in a mouse model of pancreatic cancer.

DETAILED DESCRIPTION OF THE INVENTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention. It should be noted that there are many different and alternative configurations, devices, compositions, and technologies to which the disclosed invention may be applied. The full scope of the inventions is not limited to the examples that are described below.

Compound

Herein the Inventors disclose a compound has with a formula of:

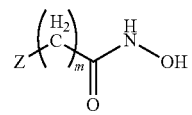

The group denoted by Z has a formula of:

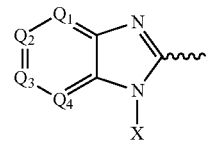

The group denoted by X may be any of H, —$C_1$-$C_6$ alkyl, aryl, —$C_3$-$C_7$ cycloalkyl or -3- to 10-membered heterocycle, any of which may be unsubstituted or substituted with one or more of the following: -halo, —$C_1$-$C_6$ alkyl, —O—($C_1$-$C_6$ alkyl), —OH, —CN, —COOR', —OC(O)R', NHR', N(R')$_2$, —NHC(O)R' or —C(O)NHR' groups wherein R' may be —H or —$C_1$-$C_6$ alkyl. The groups denoted by $Q_1$-$Q_4$ may be N or a C covalently bonded to any of the following: H, —$C_1$-$C_6$ alkyl, aryl, —$C_3$-$C_7$ cycloalkyl or 3- to 10-membered heterocycle, any of which may be unsubstituted or substituted with one or more of the following: -halo, —$C_1$-$C_6$ alkyl, —O— ($C_1$-$C_6$ alkyl), —OH, —CN, —COOR', —OC(O)R', NHR', N(R')$_2$, —NHC(O)R' or —C(O)NHR'. The groups denoted by R' may be —H or any —$C_1$-$C_6$ alkyl. The number denoted by the letter m is any integer greater than 4 or less than 11.

A —$C_1$-$C_6$ alkyl group includes any straight or branched, saturated or unsaturated, substituted or unsubstituted hydrocarbon comprised of between one and six carbon atoms. Examples of —$C_1$-$C_6$ alkyl groups include, but are not limited to methyl, ethyl, propyl, isopropyl, butyl, sec-butyl, tert-butyl, pentyl, isopentyl, neopentyl, hexyl, isohexyl, neohexyl, ethylenyl, propylenyl, 1-butenyl, 2-butenyl, 1-pentenyl, 2-pentenyl, 1-hexenyl, 2-hexenyl, 3-hexenyl, acetylenyl, pentynyl, 1-butynyl, 2-butynyl, 1-pentynyl, 2-pentynyl, 1-hexynyl, 2-hexynyl and 3-hexynyl groups. Substituted —$C_1$-$C_6$ alkyl groups may include any applicable chemical moieties. Examples of groups that may be substituted onto any of the above listed —$C_1$-$C_6$ alkyl groups include but are not limited to the following examples: halo, —$C_1$-$C_6$ alkyl, —O—($C_1$-$C_6$ alkyl), —OH, —CN, —COOR', —OC(O)R', —NHR', N(R')$_2$, —NHC(O)R' or —C(O)NHR' groups. The groups denoted R' above may be —H or any —$C_1$-$C_6$ alkyl.

An aryl group includes any unsubstituted or substituted phenyl or napthyl group. Examples of groups that may be substituted onto ay aryl group include, but are not limited to: halo, —$C_1$-$C_6$ alkyl, —O—($C_1$-$C_6$ alkyl), —OH, —CN, —COOR', —OC(O)R', NHR', N(R') 2, —NHC(O), R', or —C(O)NEtR'. The group denoted R' may be —H or any —$C_1$-$C_6$ alkyl.

A $C_3$-$C_7$ cycloalkyl group includes any 3-, 4-, 5-, 6-, or 7-membered substituted or unsubstituted non-aromatic carbocyclic ring. Examples of $C_3$-$C_7$ cycloalkyl groups include, but are not limited to, cyclopropyl, cyclobutyl, cyclopentyl, cyclopentadienyl, cyclohexyl, cyclohexenyl, cycloheptyl, cycloheptanyl, 1,3-cyclohexadienyl, -1,4-cyclohexadienyl, -1,3-cycloheptadienyl, and 1,3,5-cycloheptatrienyl groups. Examples of groups that may be substituted onto $C_3$-$C_7$ cycloalkyl groups include, but are not limited to: -halo, —$C_1$-$C_6$ alkyl, —O—($C_1$-$C_6$ alkyl), —OH, —CN, —COOR', —OC(O) R', NHR', N(R')2, —NHC(O)R' or —C(O)NHR' groups. The groups denoted R' above include an —H or any unsubstituted —$C_1$-$C_6$ alkyl, examples of which are listed above. Halo groups include any halogen. Examples include but are not limited to —F, —Cl, —Br, or —I.

A heterocycle may be any optionally substituted saturated, unsaturated or aromatic cyclic moiety wherein said cyclic moiety is interrupted by at least one heteroatom selected from oxygen (0), sulfur (S) or nitrogen (N). Heterocycles may be monocyclic or polycyclic rings. For example, suitable substituents include halogen, halogenated C1-6 alkyl, halogenated C1-6 alkoxy, amino, amidino, amido, azido, cyano, guanidino, hydroxyl, nitro, nitroso, urea, OS(O)$_2$R; OS(O)$_2$OR, S(O)$_2$OR S(O)$_{0-2}$R, C(O)OR wherein R may be H, $C_1$-$C_6$ alkyl, aryl or 3 to 10 membered heterocycle) OP(O)OR$_1$OR$_2$, P(O)OR$_1$OR$_2$, SO$_2$NR$_1$R$_2$, NR$_1$SO$_2$R$_2$C(R$_1$) NR$_2$C(R$_1$)NOR$_2$, R1 and R2 may be independently H, $C_1$-$C_6$ alkyl, aryl or 3 to 10 membered heterocycle), NR$_1$C(O)R$_2$, NR$_1$C(O)OR$_2$, NR$_3$C(O)NR$_2$R$_1$, C(O)NR$_1$R$_2$, OC(O) NR$_1$R$_2$. For these groups, R$_1$, R$_2$ and R$_3$ are each independently selected from H, $C_1$-$C_6$ alkyl, aryl or 3 to 10 membered heterocycle or R$_1$ and R$_2$ are taken together with the atoms to which they are attached to form a 3 to 10 membered heterocycle.

Possible substituents of heterocycle groups include halogen (Br, Cl, I or F), cyano, nitro, oxo, amino, $C_{1-4}$ alkyl (e.g., $CH_3$, $C_2H_5$, isopropyl) $C_{1-4}$ alkoxy (e.g., $OCH_3$, $OC_2H_5$, halogenated $C_{1-4}$ alkyl (e.g., $CF_3$, $CHF_2$), halogenated $C_{1-4}$ alkoxy (e.g., $OCF_3$, $OC_2F_5$), COOH, COO—$C_{1-4}$ alkyl, CO—$C_{1-4}$ alkyl, $C_{1-4}$ alkyl—S— (e.g., $CH_3S$, $C_2H_5S$), halogenated $C_{1-4}$ alkyl—S— (e.g., $CF_3S$, $C_2F_5S$), benzyloxy, and pyrazolyl.

Examples of heterocycles include but are not limited to azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, morpholino, oxetanyl, oxadiazolyl, oxiranyl, oxazinyl, oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazinyl, triazolyl, thiazolyl, thienyl, tetrazinyl, thiadiazinyl, triazinyl, thiazinyl, thiopyranyl furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienapyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl groups.

The disclosed compound and its intermediates may exist in different tautomeric forms. Tautomers include any structural isomers of different energies that have a low energy barrier to interconversion. One example is proton tautomers (prototropic tautomers.) In this example, the interconversions occur via the migration of a proton. Examples of prototropic tautomers include but are not limited to keto-enol and imine-enamine isomerizations. In another example illustrated graphically below, proton migration between the 1-position and 3-position nitrogen atoms of the benzimidazole ring may occur. As a result, Formulas Ia and Ib are tautomeric forms of each other:

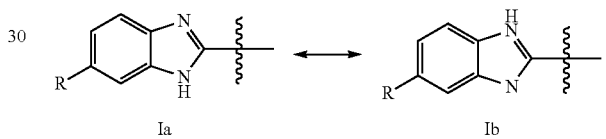

Ia    Ib

The invention further encompasses any other physiochemical or sterochemical form that the disclosed compound may assume. Such forms include diastereomers, racemates, isolated enantiomers, hydrated forms, solvated forms, or any other known or yet to be disclosed crystalline, polymorphic crystalline, or amorphous form. Amorphous forms lack a distinguishable crystal lattice and therefore lack an orderly arrangement of structural units. Many pharmaceutical compounds have amorphous forms. Methods of generating such chemical forms will be well known by one with skill in the art.

In some aspects of the invention the disclosed compound is in the form of a pharmaceutically acceptable salt. Pharmaceutically acceptable salts include any salt derived from an organic or inorganic acid. Examples of such salts include but are not limited to the following: salts of hydrobromic acid, hydrochloric acid, nitric acid, phosphoric acid and sulphuric acid. Organic acid addition salts include, for example, salts of acetic acid, benzenesulphonic acid, benzoic acid, camphorsulphonic acid, citric acid, 2-(4-chlorophenoxy)-2-methylpropionic acid, 1,2-ethanedisulphonic acid, ethanesulphonic acid, ethylenediaminetetraacetic acid (EDTA), fumaric acid, glucoheptonic acid, gluconic acid, glutamic acid, N-glycolylarsanilic acid, 4-hexylresorcinol, hippuric acid, 2-(4-hydroxybenzoyl)benzoicacid, 1-hydroxy-2-naphthoicacid, 3-hydroxy-2-naphthoic acid, 2-hydroxyethanesulphonic acid, lactobionic acid, n-dodecyl sulphuric acid, maleic acid, malic acid, mandelic acid, methanesulphonic acid, methyl sulpuric acid, mucic acid, 2-naphthalenesulphonic acid, pamoic acid, pantothenic acid, phosphanilic acid ((4-aminophenyl) phosphonic acid), picric acid, salicylic acid, stearic acid, succinic acid, tannic acid, tartaric acid, terephthalic acid, p-toluenesulphonic acid, 10-undecenoic acid or any other such acid now known or yet to be disclosed. It will be appreciated by one skilled in the art that such pharmaceutically acceptable salts may be used in the formulation of a pharmacological composition. Such salts may be prepared by reacting the disclosed compound with a suitable acid in a manner known by those skilled in the art.

The invention further encompasses aspects in which a protecting group is added to the compound. One skilled in the art would recognize that during the synthesis of complex molecules, one group on the disclosed compound may happen to interfere with an intended reaction that includes a second group on the compound. Temporarily masking or protecting the first group encourages the desired reaction. Protection involves introducing a protecting group to a group to be protected, carrying out the desired reaction, and removing the protecting group Removal of the protecting group may be referred to as deprotection. Examples of compounds to be protected in some syntheses include hydroxy groups, amine groups, carbonyl groups, carboxyl groups and thiols.

Many protective groups and reagents capable of introducing them into synthetic processes have been and are continuing to be developed today. A protecting group may result from any chemical synthesis that selectively attaches a group that is resistant to certain reagents to the chemical group to be protected without significant effects on any other chemical groups in the molecule, remains stable throughout the synthesis, and may be removed through conditions that do not adversely react with the protected group, nor any other chemical group in the molecule. Multiple protecting groups may be added throughout a synthesis and one skilled in the art would be able to develop a strategy for specific addition and removal of the protecting groups to and from the groups to be protected.

Protecting groups, reagents that add those groups, preparations of those reagents, protection and deprotection strategies under a variety of conditions, including complex syntheses with mutually complementary protecting groups are all well known in the art. Nonlimiting examples of all of these may be found in Green et al, *Protective Groups in Organic Chemistry* 2$^{nd}$ Ed., (Wiley 1991), and Harrison et al, *Compendium of Synthetic Organic Methods*, Vols. 1-8 (Wiley, 1971-1996) both of which hereby incorporated by reference in its entirety.

Racemates, individual enantiomers, or diasteromers of the disclosed compound may be prepared by specific synthesis or resolution through any method now known or yet to be disclosed. For example, the disclosed compound may be resolved into it enantiomers by the formation of diasteromeric pairs through salt formation using an optically active acid. Enantiomers are fractionally crystallized and the free base regenerated. In another example, enantiomers may be separated by chromatography. Such chromatography may be any appropriate method now known or yet to be disclosed that is appropriate to separate enantiomers such as HPLC on a chiral column.

Synthesis Methods

Different aspects of the invention may be prepared via the general synthetic procedures outlined below. It will be readily apparent to one skilled in the art know how to prepare aspects of the invention using the correct starting materials, synthetic intermediates and reagents from the exemplary procedures below.

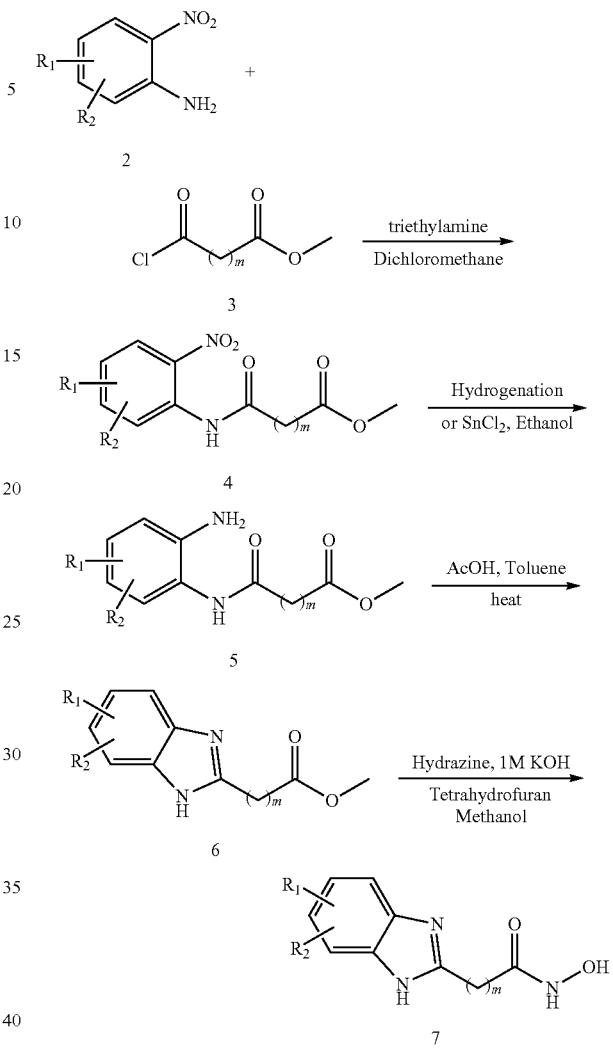

In this example, an aniline of formula 2 is coupled with an acid chloride of formula 3 in the presence of triethylamine to generate an amide of formula 4. Reduction of the amide of formula 4 using either hydrogenation or tin(II) chloride yields an aniline of formula 5. Cyclization of the analine of formula 5 with a catalytic amount of acetic acid in toluene provides a benzimidazole of formula 6, which is subsequently coupled with hydroxylamine to give a hydroxamic acid of formula 7. The group labeled R1 may be —H, -halo, —$C_1$-$C_6$ alkyl, -aryl, —$C_3$-$C_7$ cycloalkyl, or 3 to 10 membered heterocycle. The group labeled R2 may be —H, -halo, —$C_1$-$C_6$ alkyl, -aryl, —$C_3$-$C_7$ cycloalkyl, or 3 to 10 membered heterocycle. The integer m may be any integer greater than 4.

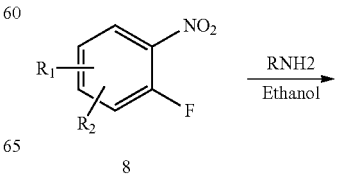

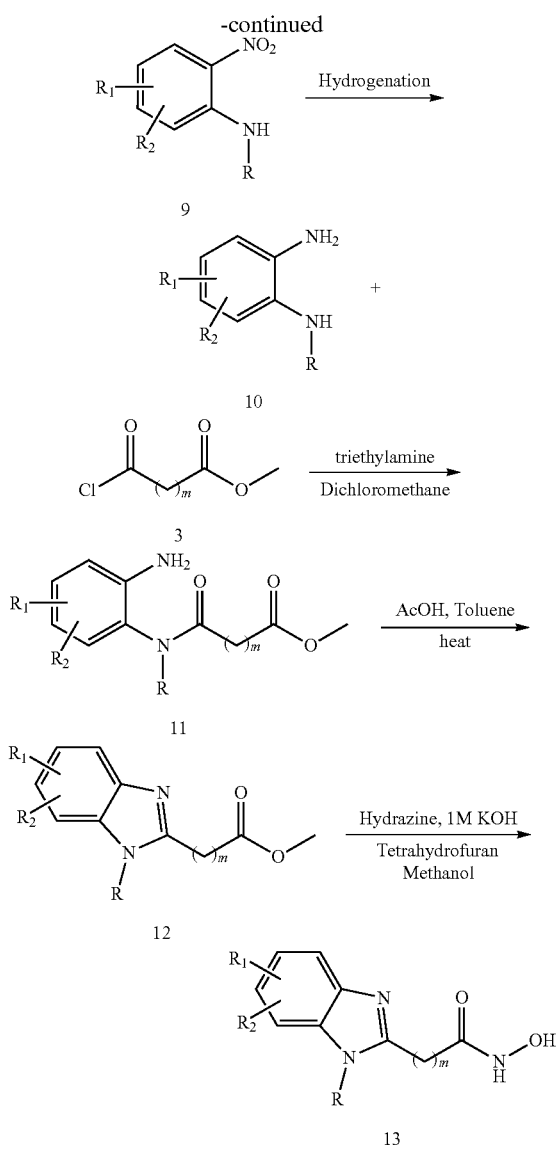

Alternatively, an amine (RNH2) reacts with a compound with a 1-fluoro-2-nitrobenzene of formula 8 gives an aniline of formula 9. Hydrogenation of the compound with the aniline of formula 9 affords an aniline of formula 10, which is coupled with an acid chloride of formula 3 in the presence of a base to yield an amide of formula 11. Cyclization of 11 with a catalytic amount of acetic acid in toluene provides a benzimidazole of formula 12. The benzimidazole of formula 12 is subsequently coupled with hydroxylamine to yield a hydroxamic acid of formula 13. The group labeled R may be any of the following: —H, -halo, —$C_1$-$C_6$ alkyl, -aryl, —$C_3$-$C_7$ cycloalkyl, or -3 to 10 membered heterocycle. The group labeled R2 may be —H, -halo, —$C_1$-$C_6$-alkyl, -aryl, —$C_3$-$C_7$ cycloalkyl, or -3 to 10 membered heterocycle. The integer m may be any integer greater than 4.

The invention further encompasses pharmaceutical compositions that include the disclosed compound as an ingredient. Such pharmaceutical compositions may take any physical form necessary depending on a number of factors including the desired method of administration and the physicochemical and stereochemical form taken by the disclosed compound or pharmaceutically acceptable salts of the compound. Such physical forms include a solid, liquid, gas, sol, gel, aerosol, or any other physical form now known or yet to be disclosed. The concept of a pharmaceutical composition including the disclosed compound also encompasses the disclosed compound or a pharmaceutically acceptable salt thereof without any other additive. The physical form of the invention may affect the route of administration and one skilled in the art would know to choose a route of administration that takes into consideration both the physical form of the compound and the disorder to be treated. Pharmaceutical compositions that include the disclosed compound may be prepared using methodology well known in the pharmaceutical art. A pharmaceutical composition that includes the disclosed compound may include a second effective compound of a distinct chemical formula from the disclosed compound. This second effective compound may have the same or a similar molecular target as the target or it may act upstream or downstream of the molecular target of the disclosed compound with regard to one or more biochemical pathways.

Pharmaceutical compositions including the disclosed compound include materials capable of modifying the physical form of a dosage unit. In one nonlimiting example, the composition includes a material that forms a coating that holds in the compound. Materials that may be used in such a coating, include, for example, sugar, shellac, gelatin, or any other inert coating agent.

Pharmaceutical compositions including the disclosed compound may be prepared as a gas or aerosol. Aerosols encompass a variety of systems including colloids and pressurized packages. Delivery of a composition in this form may include propulsion of a pharmaceutical composition including the disclosed compound through use of liquefied gas or other compressed gas or by a suitable pump system. Aerosols may be delivered in single phase, bi-phasic, or tri-phasic systems.

In some aspects of the invention, the pharmaceutical composition including the disclosed compound is in the form of a solvate. Such solvates are produced by the dissolution of the disclosed compound in a pharmaceutically acceptable solvent. Pharmaceutically acceptable solvents include any mixtures of more than one solvent. Such solvents may include pyridine, chloroform, propan-1-ol, ethyl oleate, ethyl lactate, ethylene oxide, water, ethanol, and any other solvent that delivers a sufficient quantity of the disclosed compound to treat the affliction without serious complications arising from the use of the solvent in a majority of patients.

Pharmaceutical compositions that include the disclosed compound may also include a pharmaceutically acceptable carrier. Carriers include any substance that may be administered with the disclosed compound with the intended purpose of facilitating, assisting, or helping the administration or other delivery of the compound. Carriers include any liquid, solid, semisolid, gel, aerosol or anything else that may be combined with the disclosed compound to aid in its administration. Examples include diluents, adjuvants, excipients, water, oils (including petroleum, animal, vegetable or synthetic oils,) Such carriers include particulates such as a tablet or powder, liquids such as an oral syrup or injectable liquid, and inhalable aerosols. Further examples include saline, gum acacia, gelatin, starch paste, talc, keratin, colloidal silica, and urea. Such carriers may further include binders such as ethyl cellulose, carboxymethylcellulose, microcrystalline cellulose, or gelatin; excipients such as starch, lactose or dextrins; disintegrating agents such as alginic acid, sodium alginate, Primogel, and corn starch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of carriers include polyethylene glycol, cyclodextrin, oils, or any other similar liquid carrier that may be formulated into a capsule. Still further examples of carriers include sterile diluents such as water for injection, saline solution, physiological saline, Ringer's solution, isotonic sodium chloride, fixed oils such as synthetic mono or digylcerides, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, thickening agents, lubricating agents, and coloring agents.

The pharmaceutical composition including the disclosed compound may take any of a number of formulations depending on the physicochemical form of the composition and the type of administration. Such forms include solutions, suspensions, emulsions, tablets, pills, pellets, capsules, capsules including liquids, powders, sustained-release formulations, directed release formulations, lyophylates, suppositories, emulsions, aerosols, sprays, granules, powders, syrups, elixirs, or any other formulation now known or yet to be disclosed. Additional examples of suitable pharmaceutical carriers are described in "Remington's Pharmaceutical Sciences" by E. W. Martin, hereby incorporated by reference in its entirety.

Methods of administration include, but are not limited to, oral administration and parenteral administration. Parenteral administration includes, but is not limited to intradermal, intramuscular, intraperitoneal, intravenous, subcutaneous, intranasal, epidural, sublingual, intramsal, intracerebral, iratraventricular, intrathecal, intravaginal, transdermal, rectal, by inhalation, or topically to the ears, nose, eyes, or skin. Other methods of administration include but are not limited to infusion techniques including infusion or bolus injection, by absorption through epithelial or mucocutaneous linings such as oral mucosa, rectal and intestinal mucosa. Compositions for parenteral administration may be enclosed in ampoule, a disposable syringe or a multiple-dose vial made of glass, plastic or other material.

Administration may be systemic or local. Local administration is administration of the disclosed compound to the area in need of treatment. Examples include local infusion during surgery; topical application, by local injection; by a catheter; by a suppository; or by an implant. Administration may be by direct injection at the site (or former site) of a cancer, tumor, or precancerous tissue or into the central nervous system by any suitable route, including intraventricular and intrathecal injection. Intraventricular injection can be facilitated by an intraventricular catheter, for example, attached to a reservoir, such as an Ommaya reservoir. Pulmonary administration may be achieved by any of a number of methods known in the art. Examples include use of an inhaler or nebulizer, formulation with an aerosolizing agent, or via perfusion in a fluorocarbon or synthetic pulmonary surfactant. The disclosed compound may be delivered in the context of a vesicle such as a liposome or any other natural or synthetic vesicle.

A pharmaceutical composition formulated so as to be administered by injection may be prepared by dissolving the disclosed compound with water so as to form a solution. In addition, a surfactant may be added to facilitate the formation of a homogeneous solution or suspension. Surfactants include any complex capable of non-covalent interaction with the disclosed compound so as to facilitate dissolution or homogeneous suspension of the compound.

Pharmaceutical compositions including the disclosed compound may be prepared in a form that facilitates topical or transdermal administration. Such preparations may be in the form of a solution, emulsion, ointment, gel base, transdermal patch or iontophoresis device. Examples of bases used in such compositions include opetrolatum, lanolin, polyethylene glycols, beeswax, mineral oil, diluents such as water and alcohol, and emulsifiers and stabilizers, thickening agents, or any other suitable base now known or yet to be disclosed.

Cancer cells include any cells derived from a tumor, neoplasm, cancer, precancer, cell line, or any other source of cells that are ultimately capable of potentially unlimited expansion and growth. Cancer cells may be derived from naturally occurring sources or may be artificially created. Cancer cells may also be capable of invasion into other tissues and metastasis when placed into an animal host. Cancer cells further encompass any malignant cells that have invaded other tissues and/or metastasized. One or more cancer cells in the context of an organism may also be called a cancer, tumor, neoplasm, growth, malignancy, or any other term used in the art to describe cells in a cancerous state.

Expansion of a cancer cell includes any process that results in an increase in the number of individual cells derived from a cancer cell. Expansion of a cancer cell may result from mitotic division, proliferation, or any other form of expansion of a cancer cell, whether in vitro or in vivo. Exapansion of a cancer cell further encompasses invasion and metastasis. A cancer cell may be in physical proximity to cancer cells from the same clone or from different clones that may or may not be genetically identical to it. Such aggregations may take the form of a colony, tumor or metastasis, any of which may occur in vivo or in vitro. Slowing the expansion of the cancer cell may be brought about either by inhibiting cellular processes that promote expansion or by bringing about cellular processes that inhibit expansion. Processes that inhibit expansion include processes that slow mitotic division and processes that promote cell senescence or cell death. Examples of specific processes that inhibit expansion include caspase dependent and independent pathways, autophagy, necrosis, apoptosis, and mitochondrial dependent and independent processes and further include any such processes yet to be disclosed.

Addition of a pharmaceutical composition to cancer cells includes all actions by which an effect of the pharmaceutical composition on the cancer cell is realized. The type of addition chosen will depend upon whether the cancer cells are in vivo, ex vivo, or in vitro, the physical or chemical properties of the pharmaceutical composition, and the effect the composition is to have on the cancer cell. Nonlimiting examples of addition include addition of a solution including the pharmaceutical composition to tissue culture media in which in vitro cancer cells are growing; any method by which a pharmaceutical composition may be administered to an animal including intravenous, per os, parenteral, or any other of the methods of administration; or the activation or inhibition of cells that in turn have effects on the cancer cells such as immune cells (e.g. macophages and CD8+ T cells) or endothelial cells that may differentiate into blood vessel structures in the process of angiogenesis or vasculogenesis.

Determination of an effective amount of the disclosed compound is within the capability of those skilled in the art, especially in light of the detailed disclosure provided herein. The effective amount of a pharmaceutical composition used to effect a particular purpose as well as its toxicity, excretion, and overall tolerance may be determined in cell cultures or experimental animals by pharmaceutical and toxicological procedures either known now by those skilled in the art or by any similar method yet to be disclosed. One example is the determination of the $IC_{50}$ (half maximal inhibitory concentration) of the pharmaceutical composition in vitro in cell lines or target molecules. Another example is the determination of the $LD_{50}$ (lethal dose causing death in 50% of the tested animals) of the pharmaceutical composition in experimental animals. The exact techniques used in determining an effective amount will depend on factors such as the type and physical/chemical properties of the pharmaceutical composition, the property being tested, and whether the test is to be performed in vitro or in vivo. The determination of an effective amount of a pharmaceutical composition will be well known to one of skill in the art who will use data obtained from any tests in making that determination. Determination of an effective amount of disclosed compound for addition to a cancer cell also includes the determination of an effective therapeutic amount, including the formulation of an effective dose range for use in vivo, including in humans.

Treatment is contemplated in living entities including but not limited to mammals (particularly humans) as well as other mammals of economic or social importance, including those of an endangered status. Further examples include livestock or other animals generally bred for human consumption and domesticated companion animals.

The toxicity and therapeutic efficacy of a pharmaceutical composition may be determined by standard pharmaceutical procedures in cell cultures or animals. Examples include the determination of the $IC_{50}$ (the half maximal inhibitory concentration) and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized.

The effective amount of the disclosed compound to results in the slowing of expansion of the cancer cells would preferably result in a concentration at or near the target tissue that is effective in slowing cellular expansion in neoplastic cells, but have minimal effects on non-neoplastic cells, including non-neoplastic cells exposed to radiation or recognized chemotherapeutic chemical agents. Concentrations that produce these effects can be determined using, for example, apoptosis markers such as the apoptotic index and/or caspase activities either in vitro or in vivo.

Treatment of a condition is the practice of any method, process, or procedure with the intent of halting, inhibiting, slowing or reversing the progression of a disease, disorder or condition, substantially ameliorating clinical symptoms of a disease disorder or condition, or substantially preventing the appearance of clinical symptoms of a disease, disorder or condition, up to and including returning the diseased entity to its condition prior to the development of the disease.

The addition of a therapeutically effective amount of the disclosed compound encompasses any method of dosing of a compound. Dosing of the disclosed compound may include single or multiple administrations of any of a number of pharmaceutical compositions that include the disclosed compound as an active ingredient. Examples include a single administration of of a slow release composition, a course of treatment involving several treatments on a regular or irregular basis, multiple administrations for a period of time until a diminution of the disease state is achieved, preventative treatments applied prior to the instigation of symptoms, or any other dosing regimen known in the art or yet to be disclosed that one skilled in the art would recognize as a potentially effective regimen. A final dosing regimen including the regularity of and mode of administration will be dependent on any of a number of factors including but not limited to the subject being treated; the severity of the affliction; the manner of administration, the stage of disease development, the presence of one or more other conditions such as pregnancy, infancy, or the presence of one or more additional diseases; or any other factor now known or yet to be disclosed that affects the choice of the mode of administration, the dose to be administered and the time period over which the dose is administered.

Pharmaceutical compositions that include the disclosed compound may be administered prior to, concurrently with, or after administration of a second pharmaceutical composition that may or may not include the compound. If the compositions are administered concurrently, they are administered within one minute of each other. If not administered concurrently, the second pharmaceutical composition may be administered a period of one or more minutes, hours, days, weeks, or months before or after the pharmaceutical composition that includes the compound. Alternatively, a combination of pharmaceutical compositions may be cyclically administered. Cycling therapy involves the administration of one or more pharmaceutical compositions for a period of time, followed by the administration of one or more different pharmaceutical compositions for a period of time and repeating this sequential administration, in order to reduce the development of resistance to one or more of the compositions, to avoid or reduce the side effects of one or more of the compositions, and/or to improve the efficacy of the treatment.

The invention further encompasses kits that facilitate the administration of the disclosed compound to a diseased entity. An example of such a kit includes one or more unit dosages of the compound. The unit dosage would be enclosed in a preferably sterile container and would be comprised of the disclosed compound and a pharmaceutically acceptable carrier. In another aspect, the unit dosage would comprise one or more lyophilates of the compound. In this aspect of the invention, the kit may include another preferably sterile container enclosing a solution capable of dissolving the lyophilate. However, such a solution need not be included in the kit and may be obtained separately from the lyophilate. In another aspect, the kit may include one or more devices used in administrating the unit dosages or a pharmaceutical composition to be used in combination with the compound. Examples of such devices include, but are not limited to, a syringe, a drip bag, a patch or an enema. In some aspects of the invention, the device comprises the container that encloses the unit dosage.

Pharmaceutical compositions including the disclosed compound may be used in methods of treating cancer. Such methods involve the administration of a therapeutic amount of a pharmaceutical composition that includes the disclosed compound and/or a pharmaceutically acceptable salt thereof to a mammal, preferably a mammal in which a cancer has been diagnosed.

A therapeutic amount further includes the prevention of progression of the cancer to a neoplastic, malignant or metastatic state. Such preventative use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology*, 2d Ed., W. B. Saunders Co., Philadelphia, pp. 68-79). Hyperplasia is a form of controlled cell proliferation involving an increase in cell number in a tissue or organ, without significant alteration in structure or activity. For example, endometrial hyperplasia often precedes endometrial cancer and precancerous colon polyps often transform into cancerous lesions. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype or of a malignant phenotype, displayed in vivo or displayed in vitro by a cell sample derived from a patient can indicate the desirability of prophylactic/therapeutic administration of the pharmaceutical composition that includes the compound. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84-90 for characteristics associated with a transformed or malignant phenotype). Further examples include leukoplakia, in which a benign-appearing hyperplastic or dysplastic lesion of the epithelium, or Bowen's disease, a carcinoma in situ, are pre-neoplastic lesions indicative of the desirability of prophylactic intervention. In another example, fibrocystic disease including cystic hyperplasia, mammary dysplasia, adenosis, or benign epithelial hyperplasia is indicates desirability of prophylactic intervention.

In some aspects of the invention, use of the disclosed compound may be determined by one or more physical factors such as tumor size and grade or one or more molecular markers and/or expression signatures that indicate prognosis and the likely response to treatment with the compound. For example, determination of estrogen (ER) and progesterone (PR) steroid hormone receptor status has become a routine procedure in assessment of breast cancer patients. See, for example, Fitzgibbons et al, Arch. Pathol. Lab. Med. 124:966-78, 2000. Tumors that are hormone receptor positive are more likely to respond to hormone therapy and also typically grow less aggressively, thereby resulting in a better prognosis for patients with ER+/PR+ tumors. In a further example, overexpression of human epidermal growth factor receptor 2 (HER-2/neu), a transmembrane tyrosine kinase receptor protein, has been correlated with poor breast cancer prognosis (see, e.g., Ross et al, The Oncologist 8:307-25, 2003), and Her-2 expression levels in breast tumors are used to predict response to the anti-Her-2 monoclonal antibody therapeutic trastuzumab (Herceptin®, Genentech, South San Francisco, Calif.).

In another aspect of the invention, the diseased entity exhibits one or more predisposing factors for malignancy that may be treated by administration of a pharmaceutical composition including the compound. Such predisposing factors include but are not limited to chromosomal translocations associated with a malignancy such as the Philadelphia chromosome for chronic myelogenous leukemia and t (14; 18) for follicular lymphoma; an incidence of polyposis or Gardner's syndrome that are indicative of colon cancer; benign monoclonal gammopathy which is indicative of multiple myeloma, kinship with persons who have had or currently have a cancer or precancerous disease, exposure to carcinogens, or any other predisposing factor that indicates in increased incidence of cancer now known or yet to be disclosed.

The invention further encompasses methods of treating cancer that comprise combination therapies that comprise the administration of a pharmaceutical composition including the disclosed compound and another treatment modality. Such treatment modalities include but are not limited to, radiotherapy, chemotherapy, surgery, immunotherapy, cancer vaccines, radioimmunotherapy, treatment with pharmaceutical compositions other than those which include the disclosed compound, or any other method that effectively treats cancer in combination with the disclosed compound now known or yet to be disclosed. Combination therapies may act synergistically. That is, the combination of the two therapies is more effective than either therapy administered alone. This results in a situation in which lower dosages of both treatment modality may be used effectively. This in turn reduces the toxicity and side effects, if any, associated with the administration either modality without a reduction in efficacy.

In another aspect of the invention, the pharmaceutical composition including the disclosed compound is administered in combination with a therapeutically effective amount of radiotherapy. The radiotherapy may be administered concurrently with, prior to, or following the administration of the pharmaceutical composition including the compound. The radiotherapy may act additively or synergistically with the pharmaceutical composition including the compound. This particular aspect of the invention would be most effective in cancers known to be responsive to radiotherapy. Cancers known to be responsive to radiotherapy include, but are not limited to, Non-Hodgkin's lymphoma, Hodgkin's disease, Ewing's sarcoma, testicular cancer, prostate cancer, ovarian cancer, bladder cancer, larynx cancer, cervical cancer, nasopharynx cancer, breast cancer, colon cancer, pancreatic cancer, head and neck cancer, esophageal cancer, rectal cancer, small-cell lung cancer, non-small cell lung cancer, brain tumors, other CNS neoplasms, or any other such tumor now known or yet to be disclosed.

Examples of pharmaceutical compositions that may be used in combination with the disclosed compound may include nucleic acid binding compositions such as cis-diamminedichloro platinum (II) (cisplatin), doxorubicin, 5-fluorouracil, taxol, and topoisomerase inhibitors such as etoposide, teniposide, irinotecan and topotecan. Still other pharmaceutical compositions include antiemetic compositions such as metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine and tropisetron.

Still other examples of pharmaceutical compositions that may be used in combination with the pharmaceutical composition including the disclosed compound are hematopoietic colony stimulating factors. Examples of hematopoietic colony stimulating factors include, but are not limited to, filgrastim, sargramostim, molgramostim and epoietin alfa. Alternatively, the pharmaceutical composition including the disclosed compound may be used in combination with an anxiolytic agent. Examples of anxiolytic agents include, but are not limited to, buspirone, and benzodiazepines such as diazepam, lorazepam, oxazapam, chlorazepate, clonazepam, chlordiazepoxide and alprazolam.

Pharmaceutical compositions that may be used in combination with pharmaceutical compositions that include the disclosed compound may include analgesic agents. Such agents may be opioid or non-opioid analgesic. Non-limiting examples of opioid analgesics inlcude morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam, sulindac or any other analgesic now known or yet to be disclosed.

In other aspects of the invention, pharmaceutical compositions including the disclosed compound may be used in combination with a method that involves treatment of cancer ex vivo. One example of such a treatment is an autologous stem cell transplant. In this method, a diseased entity's autologous hematopoietic stem cells are harvested and purged of all cancer cells. A therapeutic amount of a pharmaceutical composition including the disclosed compound may then be administered to the patient prior to restoring the entity's bone marrow by addition of either the patient's own or donor stem cells.

Cancers that may be treated by pharmaceutical compositions including the disclosed compoundeither alone or in combination with another treatment modality include solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms'tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Additional cancers that may be treated by pharmaceutical compositions including the disclosed compound include blood borne cancers such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

Examples that represent different aspects of the invention follow. Such examples should not be construed as limiting the scope of the disclosure. Alternative mechanistic pathways and analogous structures within the scope of the invention would be apparent to those skilled in the art.

EXAMPLES

Elements and acts in the example are intended to illustrate the invention for the sake of simplicity and have not necessarily been rendered according to any particular sequence or embodiment. The example is further intended to establish possession of the invention by the Inventors.

Nonlimiting examples illustrative of the invention include the following:

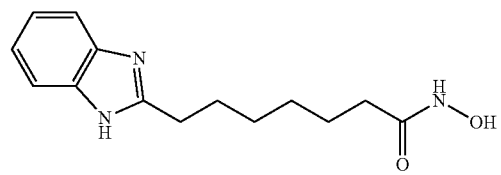

ID#14

7-(1H-benzo[d]imidazol-2-yl)-N-hydroxyheptanamide

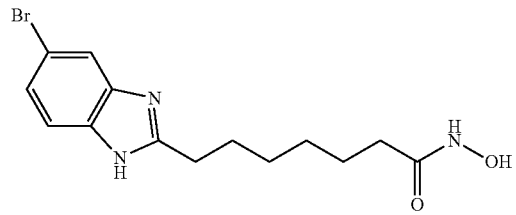

ID#15

7-(5-bromo-1H-benzimidazol-2-yl)-N-hydroxy heptanamide

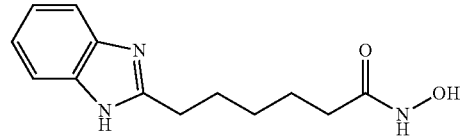

ID#16

6-(1H-benzo[d]imidazol-2-yl)-N-hydroxyhexanamide

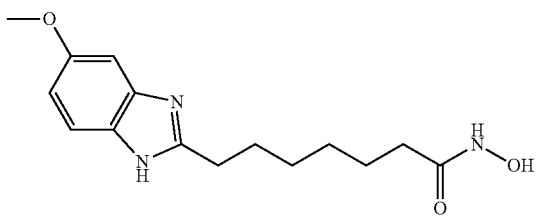

ID#17

N-hydroxy-7-(5-methoxy-1H-benzo[d]imidazol-2-yl)heptanamide

-continued

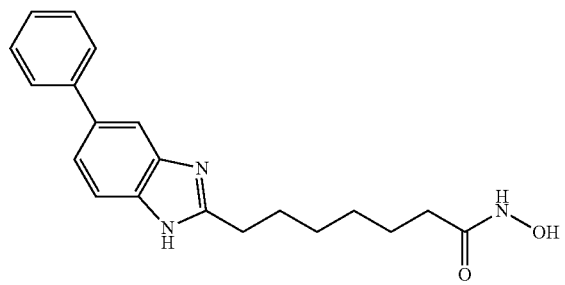

N-hydroxy-7-(5-phenyl-1H-benzo[d]imidazol-2-yl)heptanamide

ID#18

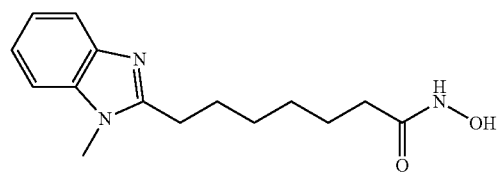

N-hydroxy-7-(1-methyl-1H-benzo[d]imidazol-2-yl) heptanamide

ID#19

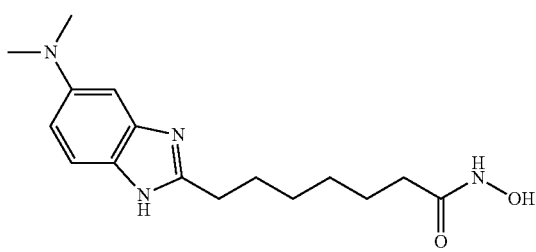

7-(5-(dimethylamino)-1H-benzo[d]imidazol-2-yl)-N-hydroxyheptanamide

ID#20

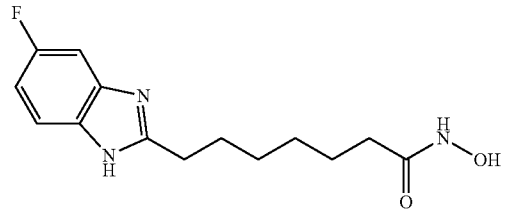

7-(5-(fluoro-1H-benzo[d]imidazol-2-yl)-N-hydroxyheptanamide

ID#21

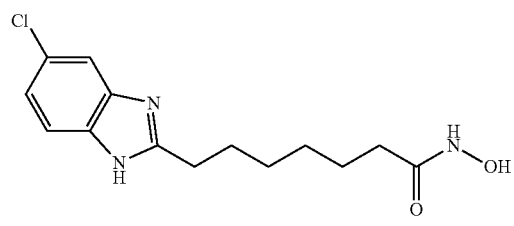

7-(5-(chloro-1H-benzo[d]imidazol-2-yl)-N-hydroxyheptanamide

ID#22

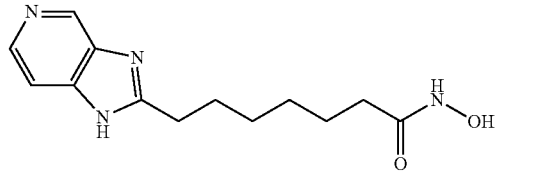

N-hydroxy-7-(3H-imidazo[4,5-c]pyridin-2-yl)heptanamide

ID#23

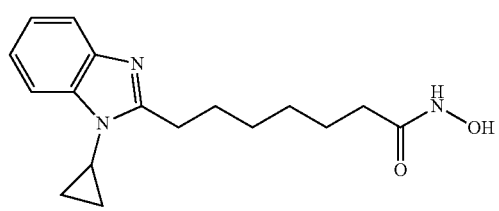

7-(1-cyclopropyl-1H-benzo[d]imidazol-2-yl)-N-hydroxyheptanamide

ID#24

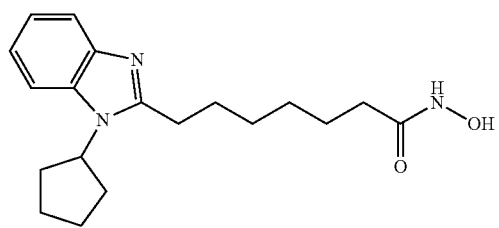

7-(1-cyclopentyl-1H-benzo[d]imidazol-2-yl)-N-hydroxyheptanamide

ID#25

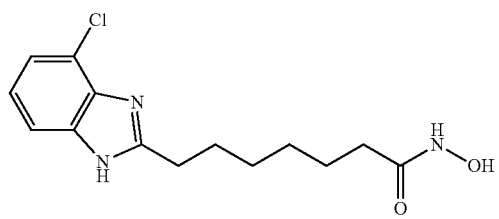

7-(4-chloro-1H-benzo[d]imidazol-2-yl)-N-hydroxyheptanamide

ID#26

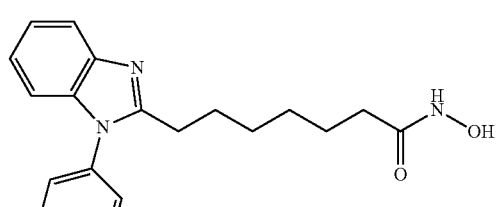

N-hydroxy-7-(1-phenyl-1H-benzo[d]imidazol-2-yl)heptanamide

ID#27

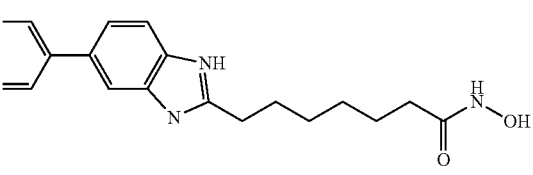

N-hydroxy-7-(5-(pyrimidin-5-yl)-1H-benzo[d]imidazol-2-yl)heptanamide

ID#28

-continued

ID#29

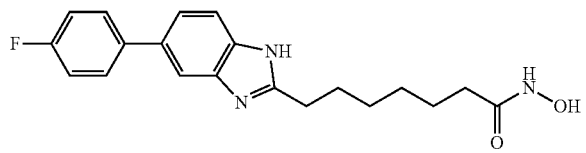

7-(5-(4-fluorophenyl)-1H-benzo[d]imidazol-2-yl)-N-hydroxyheptanamide

ID#30

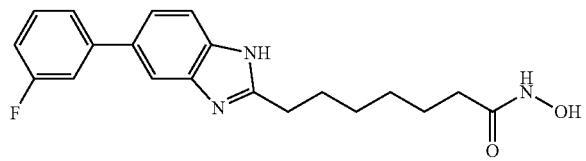

7-(5-(3-fluorophenyl)-1H-benzo[d]imidazol-2-yl)-N-hydroxyheptanamide

ID#31

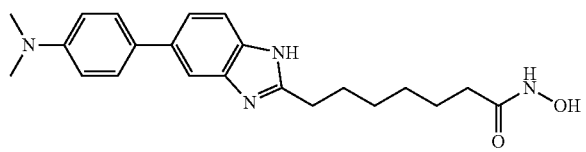

7-(5-(4-(dimethylamino)phenyl)-1H-benzo[d]imidazol-2-yl)-N-hydroxyheptanamide

ID#32

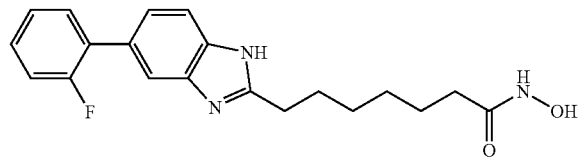

7-(5-(2-fluorophenyl)-1H-benzo[d]imidazol-2-yl)-N-hydroxyheptanamide

ID#33

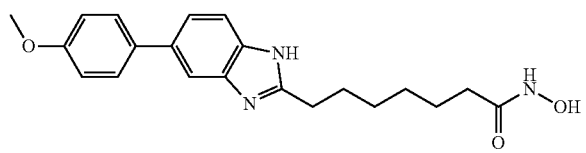

N-hydroxy-7-(5-(4-methoxyphenyl)-1H-benzo[d]imidazol-2-yl)heptanamide

Example 1

7-(5-bromo-1H-benzimidazol-2-yl)-N-hydroxy heptanamide (ID#15)

To a solution of methyl 8-chloro-8-oxooctanoate (229 mg, 1.11 mmol) in DMF at 0° C. was added a solution of 4-bromo-2-nitroaniline (200 mg, 0.922 mmol) and triethylamine (0.37 mL, 2.77 mmol) in DMF drop-wise. The reaction was stirred overnight at room temperature, diluted with ethyl acetate and washed with 1 N HCl, saturated sodium bicarbonate solution and brine. The separated organic layer was concentrated and purified by biotage column chromatography to give methyl 8-(4-bromo-2-nitrophenylamino)-8-oxooctanoate (290 mg)

To a solution of methyl 8-(4-bromo-2-nitrophenylamino)-8-oxooctanoate (241 mg, 0.623 mmol) in EtOH was added SnCl2.H2O (490 mg, 2.37 mmol). The reaction was heated to reflux overnight and quenched by water. The mixture was filtered and the filtrate was extracted with ethyl acetate. The combined organic layer was dried, concentrated and purified by biotage column chromatography to afford methyl 8-(2-amino-4-bromophenylamino)-8-oxooctanoate (149 mg)

To a solution of methyl 8-(2-amino-4-bromophenylamino)-8-oxooctanoate (140 mg, 0.395 mmol) in toluene was added a drop of acetic acid. The reaction was heated to 110° C. overnight and concentrated. The residue was purified by biotage column chromatography to give methyl 7-(5-bromo-1H-benzimidazol-2-yl)heptanoate (113 mg)

To a solution of methyl 7-(5-bromo-1H-benzimidazol-2-yl)heptanoate (100 mg, 0.295 mmol) in THF at 0° C. was added 50% hydroxylamine solution (0.17 mL, 2.70 mmol). To this was added KOH (0.74 mL, 1M in MeOH, 0.74 mmol) dropwise. The reaction was stirred at 0° C. for 2 hr, briefly concentrated and neutralized by adding 1 N HCl solution until pH was 7. The light yellow precipitate was collected by filtration and pump-dried to give 7-(6-bromo-1H-benzimidazol-2-yl)-N-hydroxy heptanamide 15 (53 mg). The filtrate was extracted with ethyl acetate, dried and concentrated. The residue was purified by column to give another portion of the desired product 15 (16 mg). LCMS (M+1 @retention time): 340@1.283 min (LC conditions: 1. Column: YMC, C-18 ODS, 50×4.6 mm 0.5 u; 2. Mobile phase: A 0.05% TFA in water and B 0.05% TFA in acetonitrile; 3. Flow rate 1.2 mL/min; Gradient program: 20% B to 100% B in 3 min).

Example 2

N-hydroxy-7-(5-phenyl-1H-benzo[d]imidazol-2-yl)heptanamide (ID#18)

To a mixture of 4-bromo-2-nitroaniline (217 mg, 1.0 mmol), phenylboronic acid (122 mg, 1.0 mmol), tetrakis-(triphenylphosphine)palladium (55 mg, 0.05 mmol) and cesium carbonate (650 mg, 2.0 mmol) was added 3 mL of ethyleneglycol dimethyl ether (DME). The reaction was heated to 80° C. and stirred under nitrogen atmosphere overnight. The mixture was filtered through a celite pad. The filtrate was concentrated and purified by biotage column chromatography to give 4-nitrobiphenyl-3-amine (207 mg)

To a solution of methyl 8-chloro-8-oxooctanoate (200 mg, 0.97 mmol) in DMF at 0° C. was added a solution of 4-nitrobiphenyl-3-amine (207 mg, 0.97 mmol) and triethylamine (0.46 mL, 3.3 mmol) in DMF drop-wise. The reaction was stirred overnight at room temperature, diluted with ethyl acetate and washed with 1 N HCl, saturated sodium bicarbonate solution and brine. The separated organic layer was concentrated and purified by biotage column chromatography to give methyl 8-(4-nitrobiphenyl-3-ylamino)-8-oxooctanoate (279 mg)

To a solution of methyl 8-(4-nitrobiphenyl-3-ylamino)-8-oxooctanoate (270 mg, 0.70 mmol) and ammonium formate (177 mg, 2.8 mmol) in methanol was added catalytic amount of palladium on carbon (5%). The mixture was heated to reflux under a nitrogen atmosphere overnight and filtered. The filtrate was concentrated and purified by biotage column chromatography to give methyl 8-(4-aminobiphenyl-3-ylamino)-8-oxooctanoate (211 mg)

To a solution of 8-(4-aminobiphenyl-3-ylamino)-8-oxooctanoate (120 mg, 0.34 mmol) in toluene was added a drop of acetic acid. The reaction was heated to 110° C. overnight and concentrated. The residue was purified by biotage column chromatography to give methyl 7-(6-phenyl-1H-benzo[d]imidazol-2-yl)heptanoate (99 mg)

To a solution of methyl 7-(6-phenyl-1H-benzo[d]imidazol-2-yl)heptanoate (50 mg, 0.15 mmol) in THF at 0° C. was added 50% hydroxylamine solution (0.10 mL, 1.5 mmol). To this was added KOH (0.45 mL, 1M in MeOH, 0.45 mmol) dropwise. The reaction was stirred at 0° C. for 2 hr, briefly concentrated and neutralized by adding 1 N HCl solution until pH was 7. The white precipitate was collected by filtration and purified by biotage column chromatography to give N-hydroxy-7-(6-phenyl-1H-benzo[d]imidazol-2-yl)heptanamide 18 (27 mg). MS (M+1=338)

Example 3

7-(1-cyclopropyl-1H-benzo[d]imidazol-2-yl)-N-hydroxyheptanamide (ID#24)

To a solution of 1-fluoro-2-nitrobenzene (0.50 g, 3.5 mmol) in ethanol was added cyclopropyl amine (0.60 g, 10.5 mmol). The solution was heated to 80° C. overnight and concentrated. The residue was purified by biotage column chromatography to give N-cyclopropyl-2-nitroaniline (0.60 g)

To a solution of N-cyclopropyl-2-nitroaniline (365 mg, 2.05 mmol) and ammonium formate (516 mg, 8.2 mmol) in methanol was added catalytic amount of palladium on carbon (5%). The mixture was heated to reflux under a nitrogen atmosphere overnight and filtered. The filtrate was concentrated and purified by biotage column chromatography to give N1-cyclopropylbenzene-1,2-diamine (296 mg)

To a solution of N1-cyclopropylbenzene-1,2-diamine (221 mg, 1.49 mmol) and triethylamine (0.3 mL, 2.2 mmol) in DMF was added a solution of methyl 8-chloro-8-oxooctanoate (260 mg, 1.3 mmol) in DMF at 0° C. drop-wise. The reaction was stirred overnight at room temperature, diluted with ethyl acetate and washed with 1 N HCl, saturated sodium bicarbonate solution and brine. The separated organic layer was concentrated to give crude methyl 8-(2-(cyclopropylamino)phenylamino)-8-oxooctanoate (390 mg)

To a solution of methyl 8-(2-(cyclopropylamino)phenylamino)-8-oxooctanoate (390 mg) in toluene was added a drop of acetic acid. The reaction was heated to 110° C. overnight and concentrated. The residue was purified by biotage column chromatography to give methyl 7-(1-cyclopropyl-1H-benzo[d]imidazol-2-yl)heptanoate (249 mg)

To a solution of methyl 7-(1-cyclopropyl-1H-benzo[d]imidazol-2-yl)heptanoate (80 mg, 0.27 mmol) in THF at 0° C. was added 50% hydroxylamine solution (0.16 mL, 2.6 mmol). To this was added KOH (0.80 mL, 1M in MeOH, 0.80 mmol) dropwise. The reaction was stirred at 0° C. for 2 hr, briefly concentrated and neutralized by adding 1 N HCl solution until pH was 7. The mixture was extracted with ethyl acetate, dried and concentrated. The residue was purified by biotage column chromatography to give 7-(1-cyclopropyl-1H-benzo[d]imidazol-2-yl)-N-hydroxyheptanamide 24 (52 mg). MS (M+1=302)

Example 4

7-(1H-benzo[d]imidazol-2-yl)-N-hydroxyheptanamide ID #14

The compound was prepared using 2-nitroaniline and otherwise by following the synthesis method of Example 2. MS (M+1=262)

Example 5

6-(1H-benzo[d]imidazol-2-yl)-N-hydroxyhexanamide ID #16

The compound was prepared from 2-nitroaniline and methyl 7-chloro-7-oxoheptanoate and otherwise by following the synthesis method of Example 2. MS (M+1=248)

Example 6

N-hydroxy-7-(5-methoxy-1H-benzo[d]imidazol-2-yl)heptanamide ID #17

The compound was prepared from 5-methoxy-2-nitroaniline and otherwise by following the synthesis method of Example 2. MS (M+1=292)

Example 7

N-hydroxy-7-(1-methyl-1H-benzo[d]imidazol-2-yl)heptanamide ID #19

The compound was prepared from N1-methylbenzene-1,2-diamine and otherwise by following the synthesis method of Example 3. MS (M+1=276)

Example 8

7-(5-(dimethylamino)-1H-benzo[d]imidazol-2-yl)-N-hydroxyheptanamide ID #20

The compound was prepared from N1,N1-dimethyl-4-nitrobenzene-1,3-diamine and otherwise by following the synthesis method of Example 2. MS (M+1=305)

Example 9

7-(5-fluoro-1H-benzo[d]imidazol-2-yl)-N-hydroxyheptanamide ID #21

The compound was prepared from 4-fluorobenzene-1,2-diamine and otherwise by following the synthesis method of Example 3. MS (M+1=280)

Example 10

7-(5-chloro-1H-benzo[d]imidazol-2-yl)-N-hydroxyheptanamide ID #22

The compound was prepared from 5-chloro-2-nitroaniline and otherwise by following the synthesis method of Example 1. MS (M+1=296)

Example 11

N-hydroxy-7-(3H-imidazo[4,5-c]pyridin-2-yl)heptanamide ID #23

The compound was prepared from pyridine-3,4-diamine and otherwise by following the synthesis method of Example 3. MS (M+1=263)

Example 12

7-(1-cyclopentyl-1H-benzo[d]imidazol-2-yl)-N-hydroxyheptanamide ID #25

The compound was prepared from cyclopentylamine and 1-fluoro-2-nitrobenzene and otherwise by following the synthesis method of Example 3. MS (M+1=330)

Example 13

7-(4-chloro-1H-benzo[d]imidazol-2-yl)-N-hydroxyheptanamide ID #26

The compound was prepared from 3-chloro-2-nitroaniline and otherwise by following the synthesis method of Example 1. MS (M+1=296)

Example 14

N-hydroxy-7-(1-phenyl-1H-benzo[d]imidazol-2-yl)heptanamide ID #27

The compound was prepared from aniline and 1-fluoro-2-nitrobenzene and otherwise by following the synthesis method of Example 3. MS (M+1=338)

Example 15

N-hydroxy-7-(5-(pyrimidin-5-yl)-1H-benzo[d]imidazol-2-yl)heptanamide ID #28

The compound was prepared from 4-bromo-2-nitroaniline and pyrimidine-5-boronic acid and otherwise by following the synthesis method of Example 2. MS (M+1=340)

Example 16

7-(5-(4-fluorophenyl)-1H-benzo[d]imidazol-2-yl)-N-hydroxyheptanamide ID #29

The compound was prepared from 4-bromo-2-nitroaniline and 4-fluorophenylboronic acid and otherwise by following the synthesis method of Example 2. MS (M+1=356)

Example 17

7-(5-(3-fluorophenyl)-1H-benzo[d]imidazol-2-yl)-N-hydroxyheptanamide ID #30

The compound was prepared from 4-bromo-2-nitroaniline and 3-fluorophenylboronic acid and otherwise by following the synthesis method of Example 2. MS (M+1=356)

Example 18

7-(5-(4-(dimethylamino)phenyl)-1H-benzo[d]imidazol-2-yl)-N-hydroxyheptanamide ID #31

The compound was prepared from 4-bromo-2-nitroaniline and 4 (dimethylamino)phenylboronic acid and otherwise by following the synthesis method of Example 2. MS (M+1=381)

Example 19

7-(5-(2-fluorophenyl)-1H-benzo[d]imidazol-2-yl)-N-hydroxyheptanamide ID #32

The compound was prepared from 4-bromo-2-nitroaniline and 2-fluorophenylboronic acid and otherwise by following the synthesis method of Example 2. MS (M+1=356)

Example 20

N-hydroxy-7-(5-(4-methoxyphenyl)-1H-benzo[d]imidazol-2-yl)heptanamide ID #33

The compound was prepared from 4-bromo-2-nitroaniline and 4-methoxyphenylboronic acid and otherwise by following the synthesis method of Example 2. MS (M+1=368)

Example 21

Cell viability in the presence of varying concentrations of the above listed aspects of the disclosed compound at different time points was used to assess cytotoxicity and the effect of the disclosed compound on cell proliferation. $IC_{50}$ (or percent activity) data for different aspects of the disclosed compound in the SKOV3 cell line are summarized in Table 1.

$IC_{50}$ (or percent activity) data for different aspects of the disclosed compound in the MiaPaCa cell line are summarized in Table 2.

$IC_{50}$ (or percent activity) data for different aspects of the disclosed compound in the mdamb231 cell line are summarized in Table 3.

$IC_{50}$ (or percent activity) data of Compound ID #15 in the H23, PANC-1, H295R, MV522, A2780, and VCAP cell lines are summarized in Table 4.

Cell viability was measured by the CellTiter-Blue® cell viability assay Promega (Madison, Wis.). This procedure measures the conversion of the indicator dye (resazurin) to resorufin, an indicator of cell viability. Following treatment, growth media was removed and cells were incubated with 20 μl of CellTiter-Blue® Reagent and growth media for 1-4 hours at 37° C. Fluorescence values were measured at 535/590 nm using a Beckman-Coulter DTX-880 microplate reader.

Cells were grown to 70% confluency, trypsinized, counted, and seeded in 96 well flat-bottom plates at a final concentration of $2.5 \times 10^3$-$5 \times 10^3$ cells/well (Day 0). Cells were allowed to incubate in growth media for 24 hours to allow for maximum adhesion. Treatment with the test agents or standard agents began on Day 1 and continued for 72 hours. At the 72 hour timepoint, treatment including media was removed. Viable cell numbers are quantified by the CellTiter-Blue® cell viability assay as described above. Experiments were repeated at least twice with the same concentrations to determine growth inhibitory activity. Results from these studies were used to calculate an $IC_{50}$ value (concentration of drug that inhibits cell growth by 50 percent of control) for each compound.

Single agent and combination studies, data from each experiment was collected and expressed as % Cell Growth using the following calculation:

$$\% \text{ Cell Growth} = (f_{test}/f_{vehicle}) \times 100$$

Where $f_{test}$ is the fluorescence of the tested sample, and $f_{vehicle}$ is the fluorescence of the vehicle in which the drug is dissolved. Dose response graphs and $IC_{50}$ values were generated using Prism 4 software (GraphPad) using the following equation:

$$Y = \frac{(Top - Bottom)}{(1 + 10^{((logIC50-X)-HillSlope)})}$$

Where X is the logarithm of concentration and Y is the response. Y starts at the Bottom and goes to Top with a sigmoid shape.

Example 22

In vivo efficacy of the disclosed compound was tested through a human pancreas tumor xenograft model. Female Ncr nude mice were inoculated with $1 \times 10^7$ MIA PaCa-2 human pancreas cells suspended in a mixture of 50% Matrigel and 50% tissue culture media in a total volume of 100 4 When the tumors reached a mean weight of 157 mg, the mice were separated into four groups of 7-8 mice per group and treated. One group was treated with vehicle only. A second group was treated with Compound ID #15 at 50 mg/kg. A third group was treated with Compound ID #15 at 100 mg/kg and a fourth group was treated with Gemcitabine at 80 mg/kg. Vehicle and Compound ID #15 were administered by mouth while Gemcitabine was administered via an intraperitoneal injection. Body weights and tumor size data were collected twice weekly. Tumor width and length were measured in millimeters and converted to tumor weight (in milligrams) using the formula (width$^2$×Length/2)=tumor weight (mg.)

Data are summarized in FIG. 1. While 50 mg/kg of Compound ID #15 was no more effective than the vehicle control in slowing growth of the xenografts, 100 mg/kg of Compound ID #15 was about as effective as gemcitabine.

TABLE 1

Skov-3 cells

| | Compound ID | | | | | | | | |
|---|---|---|---|---|---|---|---|---|---|
| | 14 | 15 | 16 | 17 | 18 | 19 | 20 | 21 | 22 | 23 |
| $IC_{50}$ (μM) | 2.7 | 0.27 | 11.0 | >10 | 0.098 | 3.0 | 1.2 | 1.9 | 0.32 | >10 |

| | Compound ID | | | | | | | | |
|---|---|---|---|---|---|---|---|---|---|
| | 24 | 25 | 26 | 27 | 28 | 29 | 30 | 31 | 32 | 33 |
| $IC_{50}$ (μM) | 9.5 | 4.8 | 10.2 | >10 | 2.6 | 1.2 | 1.5 | 6.6 | 7.4 | 3.2 |

TABLE 2

MiaPaca cells

| | Compound ID | | | | | | | |
|---|---|---|---|---|---|---|---|---|
| | 14 | 15 | 18 | 23 | 24 | 25 | 26 | 27 |
| $IC_{50}$ μM | 1.9 | 0.82 | 0.4 | >10 | 4.0 | 2.3 | 8.5 | >10 |

TABLE 3 mdamb231 cells

| | Compound ID | | | |
|---|---|---|---|---|
| | 15 | 28 | 29 | 30 |
| $IC_{50}$ μM | 0.89 | 0.54 | 0.21 | 0.33 |

TABLE 4

Compound ID #15 added to the indicated cell lines

| | Cell Line | | | | | |
|---|---|---|---|---|---|---|
| | H23 | PANC-1 | H295R | MV522 | A2780 | VCAP |
| $IC_{50}$ μM | 0.56 | 0.13 | 0.18 | 2.2 | 1.9 | 2.4 |

We claim:
1. A method of treating an animal with cancer, the method comprising the steps of:
administering an effective amount of a first pharmaceutical composition comprising a compound with the formula

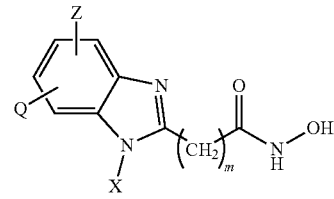

to the animal;
wherein X is selected from the group consisting of H, methyl, cyclopropyl, and cyclopentyl;
wherein Q is H;
wherein Z is selected from the group consisting of H, halo, phenyl, halophenyl, 4-methoxyphenyl, 4-dimethylaminophenyl, 5-pyrimidyl, methoxy, and dimethylamino;
wherein m is an integer selected from the group consisting of 5 and 6; and
further wherein the cancer is selected from the group consisting of ovarian cancer, breast cancer, non-small cell lung cancer, adrenocortical carcinoma, lung adenocarcinoma, and prostate cancer.
2. The method of claim 1, wherein the first pharmaceutical composition further comprises a pharmaceutically acceptable carrier.
3. The method of claim 1, wherein the animal is a human.
4. The method of claim 1 wherein the compound is selected from the group consisting of 7-(1H-benzo[d]imidazol-2-yl)-N-hydroxyheptanamide, 7-(5-bromo-1H-benzimidazol-2-yl)-N-hydroxy heptanamide, 6-(1H-benzo[d]imidazol-2-yl)-N-hydroxyhexanamide, N-hydroxy-7-(5-methoxy-1H-benzo[d]imidazol-2-yl)heptanamide, N-hydroxy-7-(5-phenyl-1H-benzo[d]imidazol-2-yl)heptanamide, N-hydroxy-7-(1-methyl-1H-benzo[d]imidazol-2-yl) heptanamide, 7-(5-(dimethylamino)-1H-benzo[d]imidazol-2-yl)-N-hydroxyheptanamide, 7-(5-fluoro-1H-benzo[d]imidazol-2-yl)-N-hydroxyheptanamide, 7-(5-chloro-1H-benzo[d] imidazol-2-yl)-N-hydroxyheptanamide, N-hydroxy-7-(3H-imidazo[4,5-c]pyridin-2-yl)heptanamide, 7-(1-cyclopropyl-1H-benzo[d]imidazol-2-yl)-N-hydroxyheptanamide, 7-(1- cyclopentyl-1H-benzo[d]imidazol-2-yl)-N-hydroxyheptanamide, 7-(4-chloro-1H-benzo[d]imidazol-2-yl)-N-hydroxyheptanamide, N-hydroxy-7-(1-phenyl-1H-benzo[d]imidazol-2-yl)heptanamide, N-hydroxy-7-(5-(pyrimidin-5-yl)-1H-benzo[d]imidazol-2-yl)heptanamide, 7-(5-(4-fluorophenyl)-1H-benzo[d]imidazol-2-yl)-N-hydroxyheptanamide, 7-(5-(3-fluorophenyl)-1H-benzo[d]imidazol-2-yl)-N-hydroxyheptanamide, 7-(5-(4-(dimethylamino)phenyl)-1H-benzo[d]imidazol-2-yl)-N-hydroxyheptanamide, 7-(5-(2-fluorophenyl)-1H-benzo[d]imidazol-2-yl)-N-hydroxyheptanamide, and N-hydroxy-7-(5-(4-methoxyphenyl)-1H-benzo[d]imidazol-2-yl)heptanamide.

5. The method of claim 4 wherein the wherein the compound is 7-(5-bromo-1H-benzimidazol-2-yl)-N-hydroxy heptanamide.

6. The method of claim 1 and further comprising administering a second treatment modality to the animal, wherein the second treatment modality is selected from the group consisting of radiotherapy, immunotherapy, and a second pharmaceutical composition.

7. A method of treating an animal with pancreatic cancer, the method comprising the steps of:
administering an effective amount of a pharmaceutical composition comprising a compound with the formula

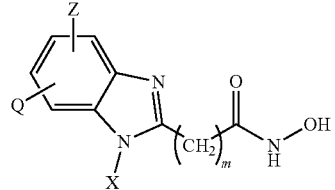

to the animal;
wherein X is selected from the group consisting of H, methyl, cyclopropyl, and cyclopentyl;
wherein Q is H;
wherein Z is selected from the group consisting of H, halo, phenyl, halophenyl, 4-methoxyphenyl, 4-dimethylaminophenyl, 5-pyrimidyl, methoxy, and dimethylamino; and
wherein m is an integer selected from the group consisting of 5 and 6.

* * * * *